US 8,216,519 B2

(12) United States Patent
Bos

(10) Patent No.: US 8,216,519 B2
(45) Date of Patent: Jul. 10, 2012

(54) ELECTRONIC CHEMICAL TRACE DETECTOR

(75) Inventor: Albert Bos, Brummen (NL)

(73) Assignee: Consultatie Implementatie Technisch Beheer B.V., Zutphen (NL)

( * ) Notice: Subject to any disclaimer, the term of this patent is extended or adjusted under 35 U.S.C. 154(b) by 164 days.

(21) Appl. No.: 12/094,675

(22) PCT Filed: Nov. 24, 2006

(86) PCT No.: PCT/NL2006/000591
§ 371 (c)(1),
(2), (4) Date: Oct. 6, 2008

(87) PCT Pub. No.: WO03/091718
PCT Pub. Date: Nov. 6, 2003

(65) Prior Publication Data
US 2009/0215180 A1 Aug. 27, 2009

Related U.S. Application Data

(60) Provisional application No. 60/750,095, filed on Nov. 28, 2005.

(30) Foreign Application Priority Data

Nov. 24, 2005 (EP) .................................. 05077694

(51) Int. Cl.
*G01N 27/18* (2006.01)
(52) U.S. Cl. ................ 422/94; 422/98; 422/90; 422/88; 422/82.12; 204/400; 204/401; 204/402; 73/23.31; 73/31.06; 340/634; 324/691; 324/724
(58) Field of Classification Search .................... 422/68, 422/98, 82.12; 73/23.31, 3.016, 424, 23, 73/19, 27; 204/400–402; 340/634; 324/691–724
See application file for complete search history.

(56) References Cited

U.S. PATENT DOCUMENTS 4,847,783 A * 7/1989 Grace et al. ...................... 422/98
4,947,057 A * 8/1990 Czarnocki et al. ............. 327/513
(Continued)

FOREIGN PATENT DOCUMENTS

GB 802372 A 10/1958
(Continued)

OTHER PUBLICATIONS

Barrettino et al. Hotplate-based Conductometric Monolithic CMOS Gas Sensor System, 2003 Symposium on V SI Circuits Digest of Technical Papers, No. 12-2,. 2003, pp. 157-160.

(Continued)

*Primary Examiner* — In Suk Bullock
*Assistant Examiner* — Sharon Pregler
(74) *Attorney, Agent, or Firm* — Leydig, Voit & Mayer, Ltd.

(57) ABSTRACT

A hotplate chemical trace detector comprising a heatable conducting plate with a heater element having a predetermined temperature-power characteristic. A balancing circuit comprises an adjustable resistor for tuning the heater element to a predefined resistor value. A processor is provided for adjusting the adjustable resistor so as to provide a stabilized temperature in said heatable conducting plate and a detection circuit is provided for detecting a change of resistance in the heatable conducting plate in accordance with the presence of a chemical trace reacting in the presence of the conducting plate. According to the invention a test circuit is provided for measuring a dissipated power in the heater element and for calculating a real temperature from the dissipated power in the heater element based on the predetermined temperature-power characteristic.

9 Claims, 3 Drawing Sheets

U.S. PATENT DOCUMENTS

2004/0075140 A1   4/2004   Baltes et al.

FOREIGN PATENT DOCUMENTS

WO   03/091718 A1   11/2003

OTHER PUBLICATIONS

International Search Report for PCT/NL2006/000591 dated Mar. 13, 2007.

* cited by examiner

ELECTRONIC CHEMICAL TRACE DETECTOR

FIELD OF THE INVENTION

The invention relates to the detection of traces in an environment, in particular, the detection of traces of volatile chemical substances in the air.

BACKGROUND

In the art, expensive equipment is used to provide detection instruments, which are also bulky since laboratory like conditions need to be provided in order to provide reliable results. Detectors which are used as field detectors and which are more economically sized exist but do require expensive calibration techniques which prevents straightforward mass production of these items. Therefore, these type of detectors are not as widely used as would be convenient, since most applications are cost prohibitive.

In the art, one detection sensor uses micro-hotplate technology, which is a semiconductor sensor on a micro-hotplate where chemical reactions occur of the traces to be detected. In particular such MOS type detector exploits the variation of electrical resistance of the sensor while, at a certain heating temperature, redox reaction take place on the surface of the sensor.

However, such hotplate technology is very sensitive to variations of the temperature and it is therefore important to provide detection of the traces at a prefixed temperature. In particular, the heater resistance is temperature dependent, which implies that current adjustments need to be provided to provide a stable temperature. This can be done by a balancing circuit which balances the heat resistor to a predefined resistor value.

U.S. Pat. No. 4,847,783 discloses a balancing circuit comprising an adjustable resistor for tuning the heater element to a predefined resistor value. The heater element operates a platinum resistance element having a predetermined resistance-temperature characteristic. However, in practice, although platinum resistance elements may show an almost perfect linear temperature behaviour, the real temperature may vary from sample to sample since the offsets of these elements may vary considerably. Thus, by presetting the heater element to a predetermined value, a repeatable yet unknown precise temperature is provided.

Hence, for different sensors, a certain chemical substance may be sensed at varying temperatures caused by the differing offsets of the heater elements, which may give rise to a differing detection results for the various sensors. Therefore, to provide a reliable sensor with replicable results, from which sensor results can be coupled to a standardized database comprising footprints of identified chemical compositions or substances, the temperature relation is very critical. However, an individual calibration setup wherein each sensor is tested in conditioned temperature and gas environments is very cumbersome.

SUMMARY OF THE INVENTION

In one aspect it is desirable to provide a sensor which obviates the need for cumbersome individual calibration actions. In another aspect it is desirable to provide a robust and stable sensor which provides reproducible data and which can be produced at relative low costs.

Accordingly there is provided a sensor according to the features of claim 1. In particular, the invention provides, in a sensor of the above described type, a test circuit for measuring a dissipated power in the heater element and for calculating a real temperature from the dissipated power in the heater element based on the predetermined power-temperature characteristic. Accordingly, a deviation of less then 1-1.5° C. from a preset temperature can be attainable using standard components. Thus it is possible to provide a low cost sensor which is easily resettable in neutral conditions. This can be typically done in a factory setting or rather by a user who needs to reset the sensor in a certain conditioned gas ambiance. In this way there is provided an automatic calibration facility on board of the sensor, which by placing it in a neutral ambiance, can easily tune the adjustable resistor to provide a real temperature.

BRIEF DESCRIPTION OF THE DRAWINGS

Further features and benefits will be apparent from the annexed description in conjunction with the drawings.

DETAILED DESCRIPTION OF THE DRAWINGS

Figure 1:
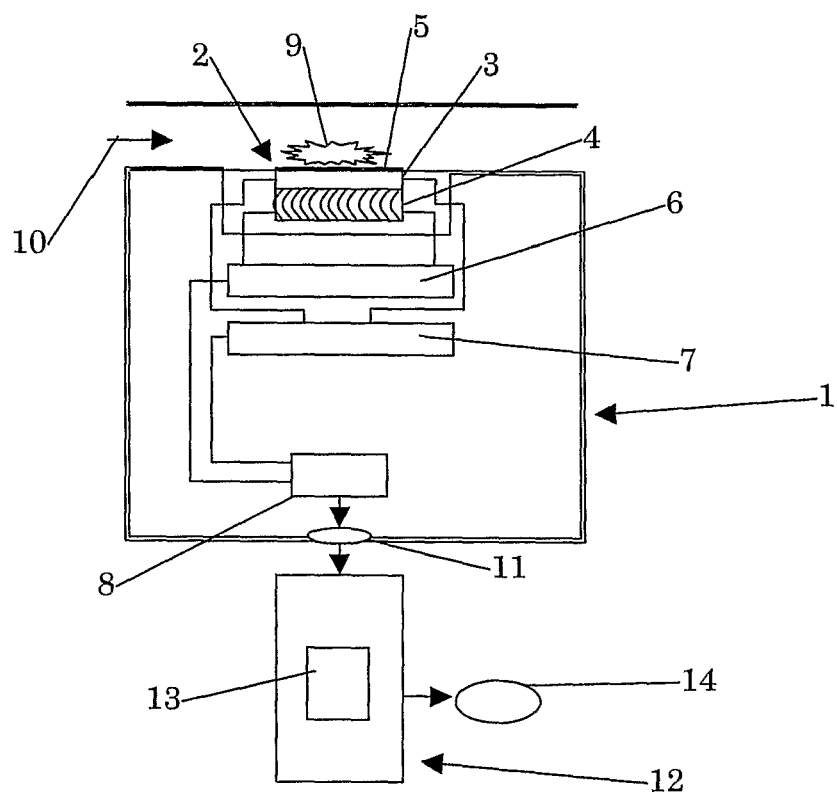
FIG. 1 shows a typical layout of the gas sensor according to the invention.

Turning to FIG. 1 a typical layout is shown for chemical trace detector 1 implementing a heatable conducting plate 2, also known as hotplate sensor 2. The hotplate sensor 2 is typically provided by a metal oxide sensor element 3 which is sensitive to chemical reactions taking place near the sensor surface area, that is in close spatial relationship with a heater element 4. This sensor element 3 shows in particular a variation in conductance depending on chemical traces reacting near the exposed surface area 5 thereof. Various metal oxide sensor elements 3 are known, including but not limited to tin oxide, zinc oxide, iron oxide and tungsten oxide sensors with or without added catalyst, including but not limited to platinum and paladium.

The hotplate 2 is heated by a heater element 4 which is preferably attached in close vicinity of the sensor element 3 produced by MEMS (micro electrical mechanical systems) technology thus ensuring an identical temperature of the conducting sensor element 3 and the heater element 4. The heater element 4 has a low thermal mass and is controlled by a processor 6 for to provide a stabilized temperature in said sensor element 3. Typically this is provided by a balancing circuit implementing a Wheatstone bridge as will be further elucidated in FIG. 4.

Furthermore, the sensor element 3 is connected to a detection circuit 7 for detecting a change of resistance in the sensor element 3 in accordance with the presence of a chemical trace reacting in the presence of the conducting plate. The output of the detection circuit 7 in connection with a preset temperature provided by the processor 6 are stored in an internal memory element 8 of the detector, which can be any type of memory, typically a flash memory.

In the memory element 8, among others, a plurality of detected resistance values in the detection circuit relative to a plurality of preset temperatures can be stored to form a footprint of a number of chemical substances 9 which are sensed by the hotplate 2 by exposing the hotplate to a flow of gas 10. Alternatively, the hotplate can be subjected to stagnant air.

In the embodiment shown, the results are stored in the memory element 8 to be transmitted via a communication terminal 11 to a base station 12 comprising a database for storing footprints of predetermined chemical substances. Thus the stored footprints can be communicated to the base station 12 comprising a database 13, for providing a best match 14 of any of said stored footprints in the memory element 8 to any of footprints stored in the database 13 of known chemical substances. In this way a particular detected composition of chemical substances can be identified in the database 13 via per se known pattern recognition and identification software techniques.

Although in this embodiment, the identification of a sensed chemical composition can be done online or offline in an external base station 12, the detector may also be equipped with specific matching routines which can match the detected footprint with one or more predefined chemical substances on board of the detector 1. In this way, the detector 1 can be easily modified to provide a detector for detecting specific predetermined chemical substances. In this (not shown) embodiment, the detector 1 hence comprises in addition a comparison circuit for comparing a stored footprint with a predetermined set of prestored footprints of predetermined chemical substances, so as to determine a particular detected chemical substance.

Figure 2:
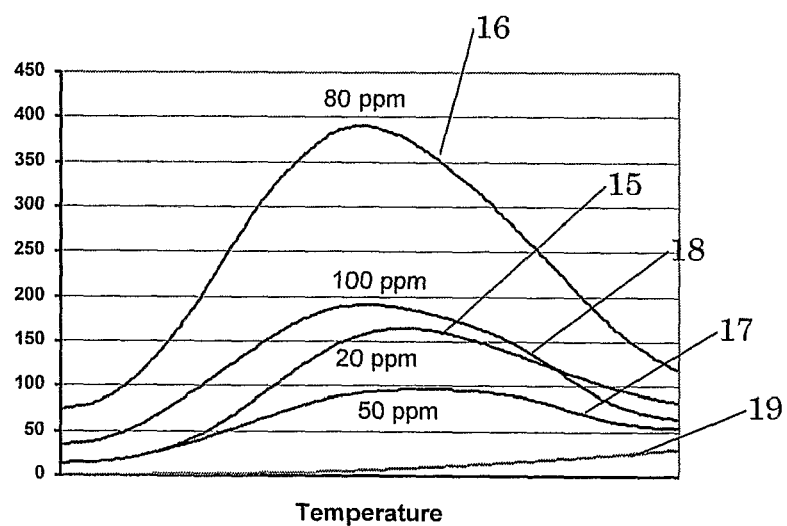
FIG. 2 shows a response characteristic of a heatable metal oxide sensor that is exposed to a variety of compositions or chemical substances in varying concentrations.

FIG. 2 shows different conductivity responses of the hotplate 2, in particular, for a concentration of 20 and 80 ppm (line 15 and 16 respectively) of toluene and for a concentration of 50 and 100 ppm (line 17 and 18 respectively) of butyl acetate. Also a blank response 19 is shown, illustrating a detected conductance for varying temperatures. The typical detection temperatures vary between 200 and 600° C. It can be shown generally that the metal oxide sensor produces peak conductance values for different chemical substances on different temperature values and for different peak values. For example, the conductance for toluene is generally higher than for butyl acetate. However, it is clear that when a precise temperature setting is unknown, the discriminatory power between 20 ppm toluene and 100 ppm butyl acetate is poor, even when a test is conducted at various temperatures. Therefore, an accurate setting of the temperature is vital for obtaining reliable test results.

Typically, the metal oxide sensor 3 is sensitive for oxygen reducible substances. Typically, components show maximum conductance according to particular temperatures settings. By obtaining the detection results at various temperature, a footprint can be obtained of the variety of chemical substances. This footprint can be compared to a number of footprints of known pure substances or mixtures that are stored in a database 13 as referred to in FIG. 1.

Figure 3:
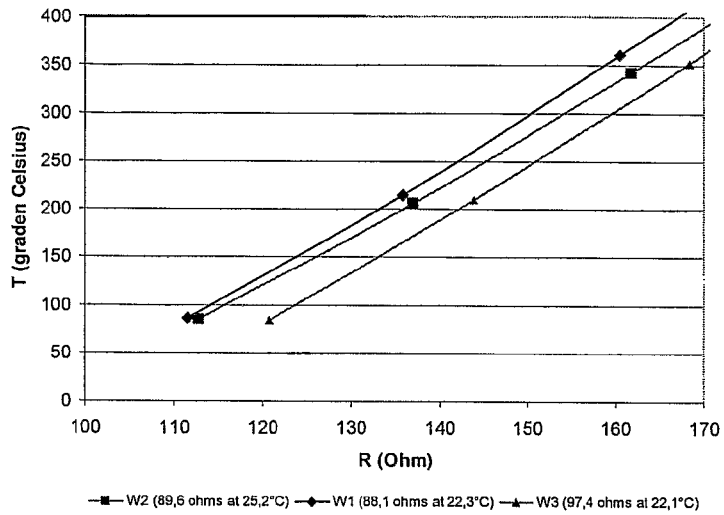
FIG. 3 shows measured resistance-temperature diagrams of three hotplate sensors.

FIG. 3 shows a measured resistance-temperature diagram of the heater element 4. As will be further elucidated with reference to FIG. 4 the heater element 4 can be integrated in a balancing circuit to preset the resistor value thereof to a predetermined value. Thus, a balancing circuit can provide a preset resistor value of the heater element 4, giving rise to a predetermined temperature according to the resistance-temperature diagram shown in FIG. 3.

However, the diagram in FIG. 3 clearly shows that the temperatures of the hotplate 2 are varying substantially for a preset resistor value. For three hotplates W1, W2, W3 shown, the hotplates W1 and W2 are of a same type. This means that the macroscopic dimensions of the heater elements 4 are almost the same. Nonetheless, where the resistance varies only 1.5 Ohm at room temperature, at a preset resistance of 160 Ohm a difference of 25° C. is provided by the heater element. It shows that without individual calibration of the heater element 4, presetting the heater element 4 to a fixed resistance can give an unacceptable spread in temperatures, which affects the reliability of the detector.

Figure 4:
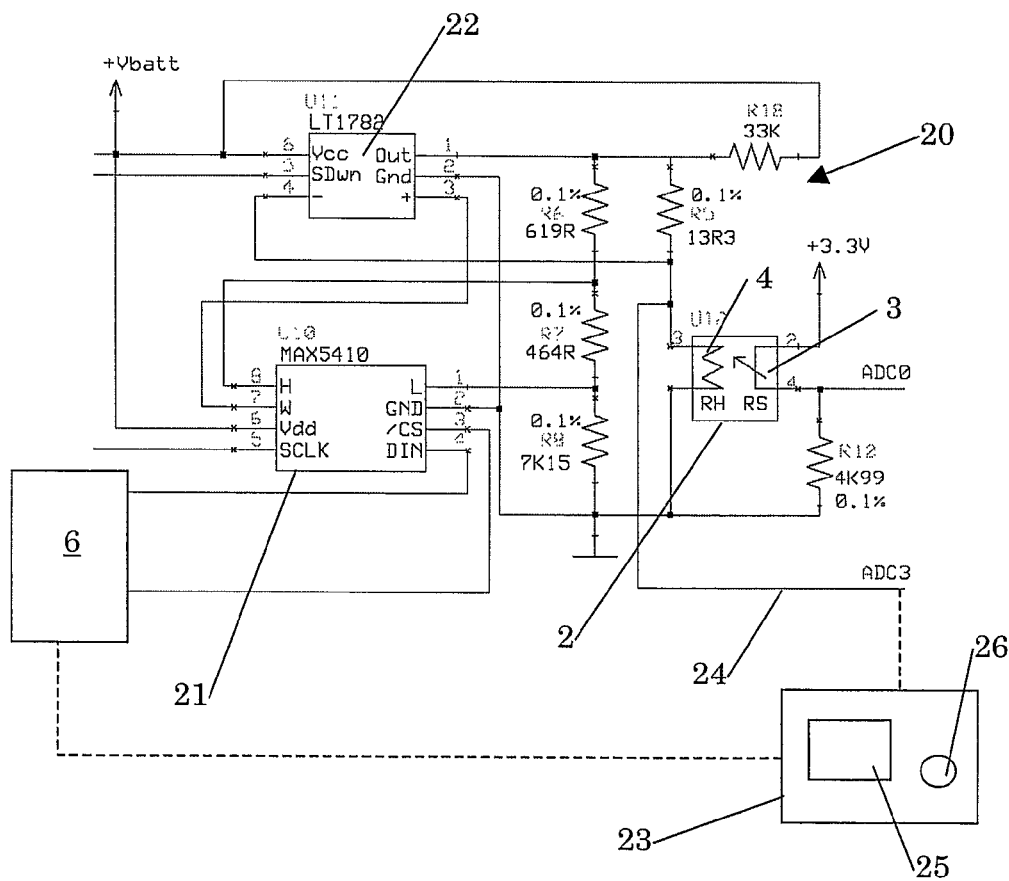
FIG. 4 shows a preferred embodiment of the inventive concept.

FIG. 4 shows a preferred embodiment of the inventive concept. In particular, FIG. 4 shows a processor 6 and a balancing circuit 20 having an adjustable resistor 21 for tuning the heater element 4 to a predefined resistor value.

The balancing circuit 20 comprises essentially a Wheatstone bridge arrangement of fixed resistors R5, R6, R7, R8, in combination with a heatable resistor 4 (also indicated in the drawing as RH) and a tunable digital potentiometer which functions as the adjustable resistor 21 (also indicated in the drawing as U10). The digital potentiometer 21 has a very good linearity. The resistance in the bridge circuit 20 is determined by the resistor R8 circuited parallel to the digital potentiometer 21. This resistor R8 (as well as the other fixed resistors R5, R6 and R7) has a very precise resistive value, typically with a margin of error of less than 0.1%. The circuit is balanced by the operational amplifier 22 (U11) which controls the voltage across the heater element 4. In particular, the amplifier U11 will control the Voltage between the + and − terminals of the amplifier so that there is no voltage difference, i.e. so that the bridge is balanced. When the Voltage difference is higher, the current through the heater element 4 (RH) will increase. The heater element 4, conducting an increased current, will heat up and the resistance will rise accordingly. Accordingly a preset resistive value of the heater element 4 can be controlled, wherein the resistive value of the heater element 4 is known expressed as a ratio of resistive values of the R5, R6, R8, and a fraction of R7 determined by tunable digital potentiometer 21 (also indicated in the drawing as U10)

Figure 5:
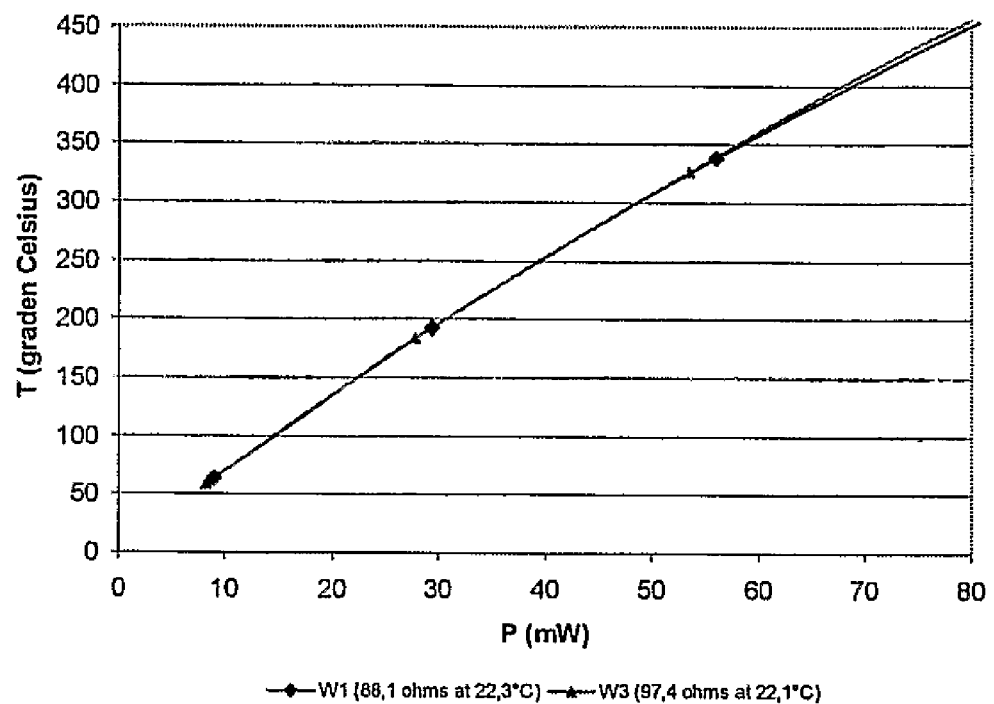
FIG. 5 shows power temperature relationships for the same heater elements as in FIG. 3.

In addition, FIG. 4 shows a test circuit 23 for the balancing circuit 20 for measuring a dissipated power in the heater element 4 and for calculating a real temperature from the dissipated power in the heater element 4 based on the predetermined power-temperature characteristic which will be further elucidated with reference to FIG. 5.

In this embodiment the test circuit 23 comprises a pair of test terminals 24 (one being grounded) that directly connect to the terminals of the heater element 4. This arrangement provides a conveniently implementable circuit 21 for calculating the power dissipation in the resistor using the familiar formula $V_H^2/R_H$ with $V_H$ being a detected voltage difference across the heater element 4. In addition, $R_H$ indicates a true resistive value of the heater element 4 derived from the balancing circuit 20.

In one embodiment, the test circuit 23 comprises a calculating circuit 25 to calculate an offset value for the digital potentiometer 21. In particular, the test circuit 23 comprises a switch 26 to activate the calculating circuit 25. In this embodiment, the test circuit 23 measures a dissipated power in predefined neutral conditions.

Upon activation, a method of calibrating the hotplate chemical trace detector 1 is carried out. In particular, using the test circuit 23 there is provided a predetermined power level to the hotplate 2 by adjusting the adjustable resistor 21. When placing the sensor is placed in a neutral ambiance the predetermined power level can be related to a set temperature using a known power-temperature characteristic of the heater plate. Thus, a precise set-point for a predetermined number of temperatures can be provided to the processor 6 for the heater element 4, thus zeroing the adjustable resistor 21 to a preset value relating to the set temperature.

In another embodiment, the test circuit is connectable to a calibration circuit for providing a lookup table to the processor 6 for calculating preset resistor values so as to provide predetermined real temperatures to said heater element. In this embodiment, the detector 1, in particular, the processor 6, may be attached to a separate a test circuit 23, for instance, in a factory setting, indicated by the dotted lines 27. In predefined neutral conditions, a series of predetermined power settings to the heater element 4 is provided by adjusting the adjustable resistor 21. Accordingly a series of predetermined temperatures to these power settings is provided using the power-temperature characteristic of the heater plate. In this way a series of setpoints for setting a temperature can be provided to form a lookup table to the adjustable resistor 21 for providing preset resistor values so as to provide predetermined real temperatures to said heater element 4. The lookup table is then integrated in the processor 6, in particular, is provided in a local memory to be accessed when setting the adjustable resistor to a predetermined temperature setting.

With the hotplate chemical trace detector as hereabove described, a precise temperature of the heater element 4 can be measured by the test circuit 23, without having to rely on the resistance-temperature characteristic of the heater element that may vary from sample to sample. In particular, a precise set point for the heater element can be provided.

Thus, when using this setpoint, a temperature can be set by adjusting the resistor in the balancing circuit to a real known temperature. The amount of power to achieve this temperature can be related to a dissipated reaction energy of the chemical trace. Indeed, the calculating circuit 25 can be arranged to calculate a difference of a measured input power from the test terminals 24 and a calculated input power. This calculated input power can for instance be provided using the known real temperature derived from the preset resistor value 21 after calibration and relating it to a calculated power in the heater element 4 using the power-temperature characteristic of the heater element 4.

In this way, a new way of characterizing chemical substances can be provided, whereas, in addition to a measured conductance of the sensing element 3.

In another embodiment, a dynamic temperature modulation is used of the hotplate 2. In this embodiment, the processor 6 is arranged to provide a sliding temperature to the heater element 4. Thus, by providing a predefined dynamic temperature profile to the heater element 4 and deriving a sensed conductance of the sensor element 3, more information can be collected from the sensor to provide it to pattern recognition software implemented in the database 13, which for this purpose stores conductance diagrams of predefined chemical substances measured in standard conditions as a function of known real temperature and temperature dynamics.

FIG. 5 shows a power-temperature characteristic for two macroscopically identically hotplate sensors 2. The term macroscopically identical indicates a generally identical geometric structure for the hotplate 2, that is, a generally identical conducting structure for conducting heat from the heater element 4 and the sensor element 3. The power-temperature characteristics for the two heater elements W1 and W2 appear to be substantially identical although heater element W1 shows a resistance of 88.1 Ohm at 22.3° C. and heater element W3 shows a resistance of 97.4 Ohms at 22.1° C., a difference of more than 10%. The power-temperature characteristic is valid in standard conditions, at room temperature in clean air. In non-standard conditions the actual temperature can be measured and used for recalculating the power-temperature characteristic. In this way, the temperature of the heater element 4 $T_{sensor}$ can be derived for a predetermined number of settings of the digital potentiometer 21 $R_{pot}$. This provides a gauge line which can be converted to a function using a linear regression.

$$Rpot = F(Tsensor) \quad [1]$$

This equation can be implemented in software operating the processor 6 so that a temperature can be preset with a deviation which may be less than 3-5° C.

Although the invention has been set forth using a limited number of embodiments the skilled person will appreciate that various modifications and adaptations thereto are possible without departing from the scope of the invention. For instance, it is possible to derive the power dissipated in the heater element by a test circuit 23 coupled more indirectly to the heater element, for instance a terminal that measures the output voltage of the amplifier U11 of FIG. 4. Alternatively, or in addition the test circuit 23 that does not need to use the balancing circuit 20 but could measure the resistance of the heater directly using a preset value of the digital potentiometer 21.

The invention is not limited to the disclosure of the embodiments shown in the description but encompasses variations and modifications thereto and is determined by the scope of the annexed claims and their equivalents.

The invention claimed is:

1. A hotplate chemical trace detector comprising:
   a heatable conducting plate comprising a heater element having a predetermined power—temperature characteristic relating a dissipated power in the heater element to a real temperature;
   a balancing circuit comprising an adjustable resistor for tuning the heater element to a predefined resistor value;
   a processor for adjusting the adjustable resistor so as to provide a stabilized temperature in said heatable conducting plate;
   a detection circuit for detecting a change of resistance in the heatable conducting plate in accordance with the presence of a chemical trace reacting in the presence of the conducting plate; and
   a test circuit for calculating the real temperature based upon a dissipated power in the heater element and the predetermined power—temperature characteristic, the test circuit comprising:
      a power measurement subcircuit adapted to measure the dissipated power in the heater element;
      a storage subcircuit adapted to store the predetermined power—temperature characteristic; and
      a calculating subcircuit coupled to the power measurement subcircuit, the calculating subcircuit adapted to determine the real temperature from the dissipated power measurement provided by the power measurement subcircuit and the predetermined power—temperature characteristic provided by the storage subcircuit.

2. The hotplate chemical trace detector according to claim 1, wherein the test circuit is connectable to a calibration circuit for providing a lookup table to the processor for providing preset resistor values so as to provide predetermined real temperatures to said heater element.

3. The hotplate chemical trace detector according to claim 1, wherein the test circuit is coupled to a processor to calculate a dissipated reaction energy of the chemical trace as a difference in a measured input power and a calculated input power from the preset resistor value after calibration.

4. The hotplate chemical trace detector according to claim 1 wherein the processor is arranged to provide a dynamic temperature profile to the heater element.

5. The hotplate chemical trace detector according to claim 1, wherein the test circuit comprises a pair of test terminals that directly connect to a pair of terminals of the heater element.

6. The hotplate chemical trace detector according to claim 1, wherein the trace detector comprises a memory for storing at least a plurality of detected resistance values in the detection circuit relative to a plurality of preset temperatures to form a footprint of a number of chemical substances.

7. The hotplate chemical trace detector according to claim 6, wherein the trace detector comprises a communication terminal for communicating the stored footprints with a database storing footprints of predetermined chemical substances, for providing a best match of said footprints to any of said stored footprints so as to determine a particular detected chemical substance.

8. The hotplate chemical trace detector according to claim 6, wherein the trace detector comprises a comparison circuit for comparing a stored footprint with a predetermined set of prestored footprints of predetermined chemical substances, so as to determine a particular detected chemical substance.

9. The hotplate chemical trace detector according to claim 1 wherein the heatable conducting plate comprises a MOS sensor.

\* \* \* \* \*

UNITED STATES PATENT AND TRADEMARK OFFICE
CERTIFICATE OF CORRECTION

PATENT NO. : 8,216,519 B2
APPLICATION NO. : 12/094675
DATED : July 10, 2012
INVENTOR(S) : Albert Bos Page 1 of 1

It is certified that error appears in the above-identified patent and that said Letters Patent is hereby corrected as shown below:

Title page

Item (87) "WO03/091718" and "Nov. 6, 2003" should be --WO 2007/061294-- and --May 31, 2007--.

Signed and Sealed this
Twenty-third Day of October, 2012

David J. Kappos
*Director of the United States Patent and Trademark Office*